United States Patent [19]

Ehrfeld et al.

[11] 4,205,913
[45] Jun. 3, 1980

[54] DETERMINATION OF THE PARTIAL PRESSURE AND THE CONCENTRATION OF A GAS

[75] Inventors: Wolfgang Ehrfeld, Ettlingen; Gunther Krieg, Karlsruhe, both of Fed. Rep. of Germany

[73] Assignee: Kernforschungszentrum Karlsruhe GmbH, Karlsruhe, Fed. Rep. of Germany

[21] Appl. No.: 917,797

[22] Filed: Jun. 22, 1978

[30] Foreign Application Priority Data

Jun. 22, 1977 [DE] Fed. Rep. of Germany ....... 2727976

[51] Int. Cl.² .......................................... G01N 21/24
[52] U.S. Cl. ..................................... 356/72; 250/340;
250/343; 356/51; 356/434
[58] Field of Search ................. 250/339, 340, 343–346;
356/51, 414, 418, 419, 72, 73, 434, 437

[56] References Cited

U.S. PATENT DOCUMENTS

| | | | |
|---|---|---|---|
| 3,979,589 | 9/1976 | Sternberg et al. | 250/345 X |
| 4,132,481 | 1/1979 | Ford et al. | 356/325 |

*Primary Examiner*—F. L. Evans
*Attorney, Agent, or Firm*—Spencer & Kaye

[57] ABSTRACT

For determining the partial pressure and concentration of a measuring gas which is in mixture with at least one additional gas according to an optical absorption technique, in which a beam of light having a predetermined intensity and alternatingly and cyclically having a first spectral distribution in which the light intensity will be reduced by passage through the measuring gas and a second spectral distribution in which the light intensity will not be reduced by passage through the measuring gas, is passed through such a mixture and its radiation intensity after passage through the mixture is measured in a radiation detector having an active element which is heated by the radiation and which produces an output representative of its degree of heating and composed of alternating measuring signal segments, resulting, respectively, from light having the first and the second spectral distribution, and adjacent signals segments are processed in order to compensate for various interference effects, the detector output is delivered to an input amplifier having a large signal to noise ratio, and signal inaccuracies due to superimposition of each signal segment portion produced by heating of the active element on a component representing the cooling behavior which the element would experience after the preceding heating period if further heating did not occur are compensated by integrating, in an integration member, successive portions of the detector output with respect to an integration base which has a fixed value relative to the detector output value corresponding to a constant active element temperature.

19 Claims, 6 Drawing Figures

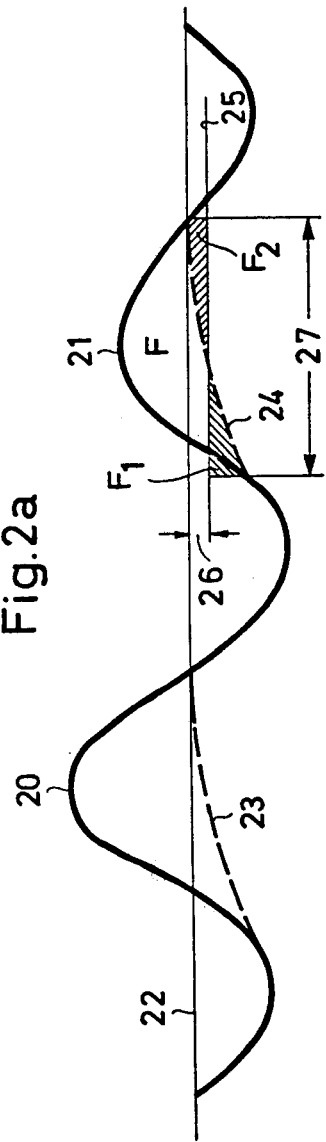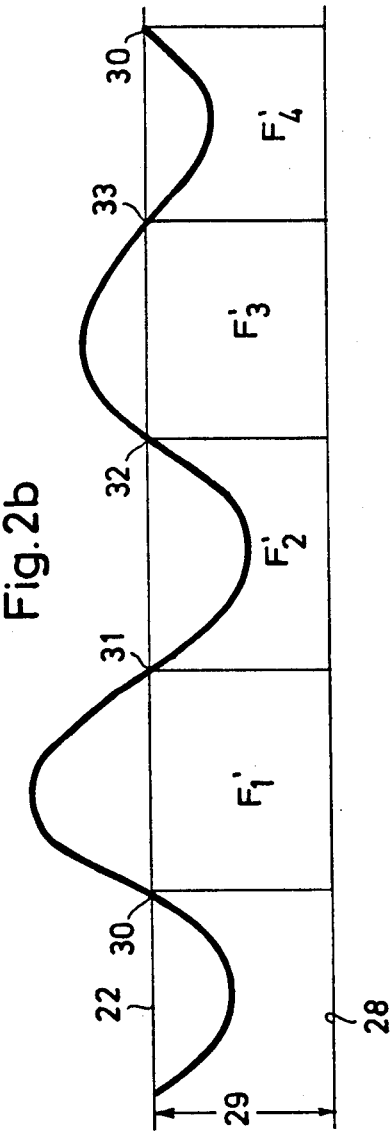

R = reference
S = sample

DETERMINATION OF THE PARTIAL PRESSURE AND THE CONCENTRATION OF A GAS

BACKGROUND OF THE INVENTION

The present invention relates to a method and circuit arrangement for determining the partial pressure and the concentration of a gas, termed a measuring gas, which is mixed with at least one additional gas according to the optical absorption method.

In such methods, defined wavelength ranges are alternatingly filtered out of a beam of light of predetermined intensity by means of filters and when the light penetrates a gas to be measured, the intensity of light in a first wavelength range and/or ranges is reduced while that of light in a second wavelength range and/or ranges is not reduced. The intensity of the light radiation is measured with a radiation sensitive detector and fluctuations in output intensity from the light source, variations in the optical transmission and reflection parameters of the beam path, and other interfering values are substantially eliminated from the measurement result by way of comparison of two successive signals having different spectral distributions.

In procedures for optimizing separation nozzle systems, separating experiments operating at low inlet pressures, under small cut and employing low $UF_6$ concentrations, i.e. very low $UF_6$ partial pressures, are achieving increasing significance.

The cut $\theta_u$ of a separation nozzle system which splits an $UF_6$ stream L into an inner partial stream Li and an outer partial stream Lo is $L_i/L$.

Moreover, it has been found that, for safety reasons, continuous control of the effectiveness of $UF_6$ low temperature separation is absolutely necessary in the case of separators operating with $UF_6$ partial pressures below $10^{-4}$ Torr. Additionally, it is desirable, in order to accurately determine the costs for separator systems, to effect continuous measurements of the HF content of the gas being processed.

The known nonselective measuring methods, however, are incapable of providing a precise $UF_6$ concentration determination at extremely low $UF_6$ partial pressures because the resulting measuring signal value is determined almost exclusively by the additional gas, which is hydrogen or helium, and which is present in excess amounts. Moreover, the measured value is falsified by gaseous impurity components, e.g. hydrogen fluoride and other compounds contained in commercial $UF_6$, which are particularly noticeable at low partial pressures. For these reasons, it is necessary to use selective measuring systems which permit separate measurements of the $UF_6$ partial pressure and of the partial pressures of the impurity components.

In a known selective process, which is constituted by the photometer process based on the bifrequency principle, the sample contained in a cuvette system is illuminated with light which alternates between two different, but closely adjacent, wavelength ranges, one of the wavelength ranges coinciding with an absorption band of the gas component to be examined and the other wavelength range lying outside of the absorption range so that light therein is not weakened, or attenuated, by the gas. The two wavelength ranges are extracted out of the spectrum of the radiation source by means of gas filters or solid state interference filters. Pulses of light, which alternate between the two wavelength ranges, pass through the cuvette system and are detected by a detector. By comparing every two successive signals produced by light of respectively different wavelengths, fluctuations in the intensity of the light source output or variations in the optical transmission and reflection properties of the beam path are substantially eliminated, as are fluctuations in the sensitivity and the zero point of the detector and variations in background radiation, since they have almost the same effect on successive radiation pulses.

The drawbacks of this process are in particular that for some measuring problems, e.g. in connection with $UF_6$ analysis, it is necessary to effect complicated dry gas rinsing of optical path outside of the analyzer chamber in order to eliminate e.g. the $H_2O$ bands, since, on the one hand, the $H_2O$ spectrum does not have the requisite gap in the region of the $\nu_3$ band of $UF_6$ and, on the other hand, the light path through air associated with a bifrequency grid analyzer is, in principle, relatively long.

Moreover, the measuring time of the grid analyzer is determined by the time required to switch between the two wavelength ranges required by the bifrequency principle. Due to the high accuracy with which the wavelengths must be selected, the switching frequency is about $10^{-2}$ Hz, so that the measuring times can be no less than about 100 seconds.

In contradistinction to the grid analyzers, quasi-continuous measurements are possible in principle within less than 1 second and over light paths which extend only a short distance through air, if the wavelength selection is effected by means of solid state filters disposed on a filter wheel which rotates, or a pendulum disc which swings, at a comparatively high frequency.

Such measuring problems can also be solved by use of known spectral analyzers with negative gas filtration, in which case gas filters and reference filter cells disposed on a rotating circular disc are moved alternatingly through the beam path.

The drawback of these methods is that they require high chopper frequencies which result in a time overlap between successive signals, producing measuring errors or even making useful measurements impossible.

In known infrared analyzers it has been attempted to avoid this problem by employing a double chopper system. In this case, the very low frequency of the filter chopper, which is lower than the reciprocal of the relaxation period of the thermal detector is used to switch between the two wavelength ranges while additionally the second chopper effects a high frequency interruption of the radiation. However, this arrangement requires a large amount of mechanical components to synchronize the two choppers. Additionally, due to wear of the mechanical components, there will occur temporary changes in synchronization so that long-term stability, which is required for many practical problems, cannot be attained. Furthermore, the signals produced during the switching period of the lower frequency chopper cannot be used for evaluation, i.e. the information furnished by the optical portion of the device is utilized only in part.

SUMMARY OF THE INVENTION

It is therefore an object of the present invention to eliminate such a second chopper and to make possible operation with high chopper frequencies which permit continuous measurements of the $UF_6$ partial pressure and of the $UF_6$ concentration with response times below one second and simultaneously with a high signal to noise ratio, high sensitivity, and, particularly, at low $UF_6$ partial pressures.

A more specific object of the invention is to perform measurements in the far infrared range at wavelengths above $4\mu$ so that effective use can be made of $UF_6$ bands which are heavily absorbing at $16\mu$, and high zero point stability as well as high reproduceability are assured.

These and other objects are achieved, according to the invention, in a method for determining the partial pressure and concentration of a measuring gas which is in mixture with at least one additional gas according to an optical absorption technique, which method includes producing a beam of light having a predetermined intensity, filtering the beam to alternatingly and cyclically give the light a first spectral distribution in which the light intensity will be reduced by passage through the measuring gas and a second spectral distribution in which the light intensity will not be reduced by passage through the measuring gas, passing the filtered beam through such a mixture, measuring the radiation intensity of the beam after passage through the mixture in a radiation detector having an active element which is heated by the radiation and which produces an output representative of its degree of heating, the output being composed of successive measuring signal segments, resulting from light having the first spectral distribution, alternating with successive reference signal segments, resulting from light having the second spectral distribution, and processing adjacent measuring signal and reference signal segments in order to compensate for fluctuations in the light beam being produced, variations in the light transmission and reflection properties of the beam path and other interference effects, by the improvement wherein the step of processing includes supplying the detector output to an input amplifier having a large signal to noise ratio, and compensating for signal inaccuracies due to superimposition of each signal segment portion produced by heating of the active element on a component representing the cooling behavior which the element would experience after the preceding heating period if further heating did not occur.

According to a first preferred embodiment of the invention, the compensating step is performed by integrating, in an integration member, each measuring signal occurring during a period when the element is being heated by the radiation, which integration is performed with respect to an integration base, applying to the integration member a direct voltage whose value determines the integration base; and adjusting the direct voltage to a magnitude which will cause the integral of a measuring signal, with respect to the integrator base, to have a value of zero when light having the first spectral distribution experiences maximum intensity reduction upon passage through such measuring gas.

The objects according to the invention are further achieved by apparatus for carrying out the above methods and including signal processing means arranged for compensating for signal inaccuracies due to superimposition of each signal segment portion produced by heating of the active element on a component representing the cooling behavior which the element would experience after the preceding heating period if further heating did not occur, composed of an analog computer stage containing an input amplifier having a large signal to noise ratio and connected to receive the detector output; a digital control unit connected for controlling the operation of the computer stage; a first indicator unit connected to the computer stage for providing an indication of the partial pressure of the measuring gas in a container; and a second indicator connected to the computer stage for providing an indication of the concentration of the measuring gas in the container.

BRIEF DESCRIPTION OF THE DRAWINGS

FIG. 2a is a waveform diagram illustrating the principle of separation of overlapping output signals from a beam detector which effects halfwave evaluation.

FIG. 2b is a waveform diagram illustrating the principle of separation of overlapping output signals from a beam detector with full wave evaluation.

DESCRIPTION OF THE PREFERRED EMBODIMENTS

Figure 1:
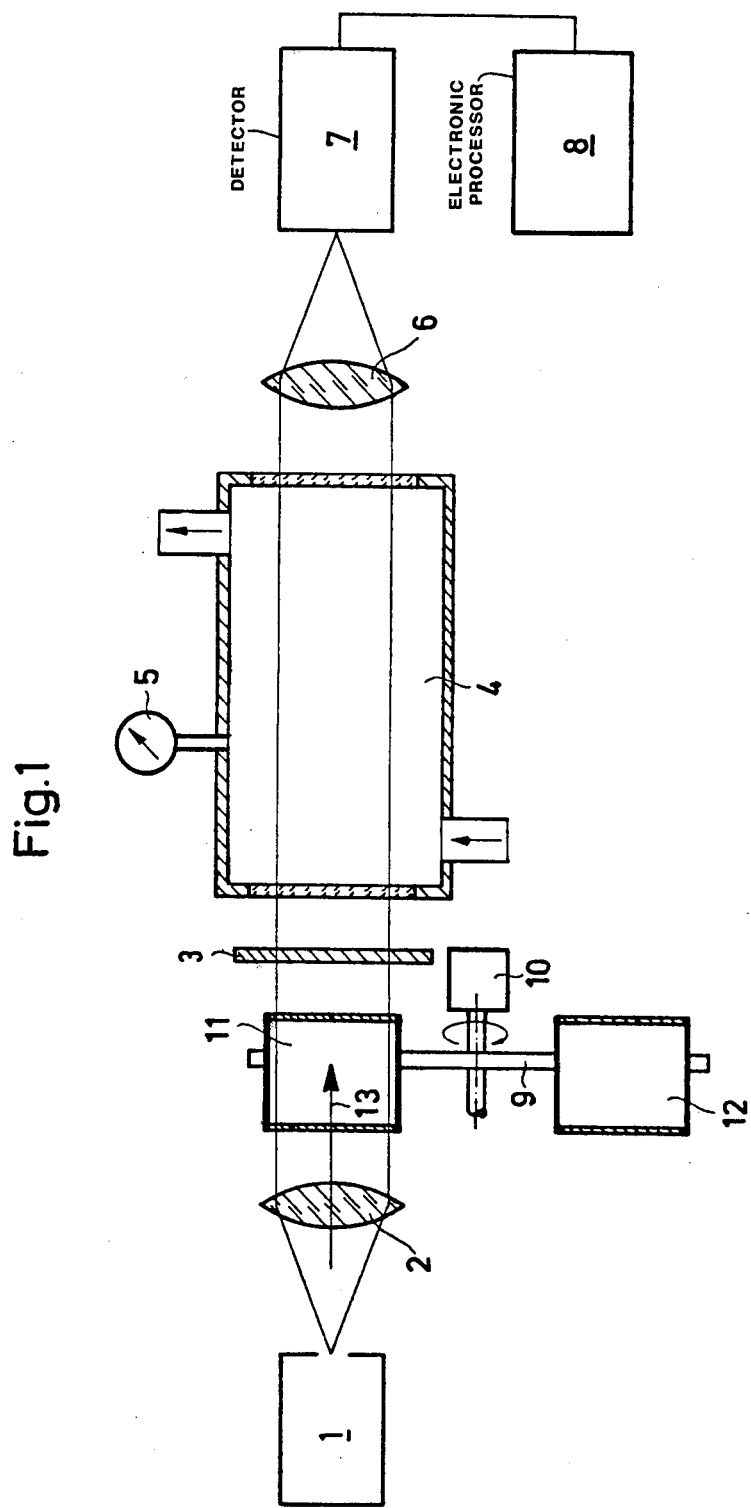
FIG. 1 is a schematic representation of a preferred embodiment of an infrared analyzer according to the invention with rotating gas or solid filters.

The basic structure of an infrared analyzer for effecting measurements according to the invention is shown in FIG. 1. The radiation emitted by an infrared radiation source 1 is directed through a first lens system 2 which forms the radiation into an approximately parallel beam, an optical broadband filter 3 which filters out the major portion of the light frequencies not required for the absorption measurements, a measuring cuvette 4 through which the measuring gas flows and whose gas pressure is measured by a pressure gauge 5, and a second lens system 6 which focusses the beam onto a radiation detector 7 which is connected in series with an electronic measuring value processor 8.

Between the first lens system 2 and the broadband filter 3, a filter wheel 9 is disposed in the beam path to act as a chopper. It is driven by a stepping motor 10 and is equipped with gas filters and/or solid interference filters. If gas filters are used, these include a reference filter 11 filled with at least one gaseous component, under high partial pressure, of a gas mixture to be examined and a measuring filter 12 which is evacuated or filled with a gas which does not absorb radiation, such as helium, for example.

In the illustrated position of filter wheel 9, the IR beam 13 penetrates reference filter 11 which is filled with the gases to be measured so that light impinging on detector 7 is reduced by the component absorbed in reference filter 11.

For HF-detection a specific example of the gas filling of reference filter 11 is 1oo Torr HF and 66o Torr He. The broadband filter 3 is selected to be one whose transmission band covers at least one absorption band of the gas to be measured. If measuring filter 12 is introduced into the beam path of the IR beam 13, the light impinging on detector 7 is reduced by the component absorbed by the measuring gas in cuvette 4 since the measuring filter 12 itself permits the beam to pass unattenuated. From the difference in intensity between the two light signals impinging on detector 7 the concentration and the partial pressure of the gas flowing through measuring cuvette 4 can be determined.

The gas mixture in cuvette 4 consists of an $H_2/UF_6/HF$ mixture. The components $UF_6$ and HF are subjected to the concentration and partial pressure determination.

When interference filters constituted by solid bodies are used the transmission curve of the first filter is made to coincide with the absorption band of the gas to be examined, the transmission curve of the second filter is placed as close to that of the first filter as possible, and the broadband filter 3 can be eliminated.

Figure 5:
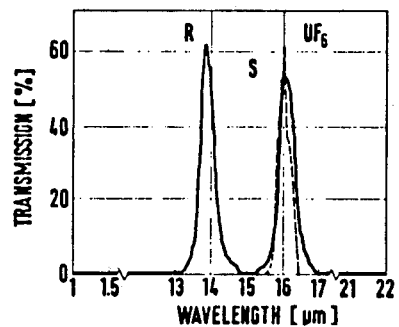
FIG. 5 shows transmission characteristics of sample and reference interference filters.

An example of the filter transmission curves for $UF_6$ measurements is given in FIG. 5.

For precise measurements of the partial pressures and of the concentrations of gas mixtures, the signal to noise ratio of the detector must be made as large as possible, independently of the measuring principle employed. This will occur if the feedback resistance $R_f$ or the source impedance $R_s$ of the preamplifier associated with the detector is very high since the signal to noise ratio S/R varies according to the relationship:

$$S/R \sim (R_f,_s)^{1/2} \quad (1)$$

However, there are limits to the values of $R_f$ or $R_s$, respectively, since the limit frequency $\nu_g$ of the amplifier system decreases, with increasing $R_f$ and with a system capacitance C, according to the relationship:

$$\nu_g \sim 1/(R_f,_s C) \quad (2)$$

so that there will occur an undesirable overlapping of successive signals in time.

The present invention resolves these conflicting considerations by setting a very high signal to noise ratio by way of a very high feedback resistance $R_f$ and/or a very high source impedance $R_s$ according to relationship (1) and then electronically eliminating the overlapping of successive signals occurring due to relationship (2). In this way it is possible to realize signal to noise ratios which are higher than was heretofore possible by a factor of 100.

FIG. 2a shows the principle of separating overlapping output signals from a radiation detector 7 for half-wave evaluation. In the selected example, detector 7 is a thermal detector for IR radiation. However, it is just as applicable for every other detector type if there is overlapping of signals. As a result of rotation of filter wheel 9 of the apparatus of FIG. 1, reference signals 20 and measuring signals 21 are generated alternatingly and appear as positive or negative signals with reference to a zero amplitude line 22. The total output signal shown in FIG. 2a is proportional to the time rate of temperature change, dT/dt, of the active element of detector 7, i.e. high positive signal values indicate strong heating, negative signal values correspond to cooling of the detector. The zero amplitude line 22, therefore, corresponds to a steady temperature of the active detector element.

The dashed curve sections 23 and 24 represent the cooling behavior which the detector would experience if the respective next following radiation pulse did not impinge on the detector until after an infinitely long time.

In view of the relationship (2), however, the temperature rise curve of the next radiation pulse is superimposed on curve sections 23, 24. The actual measuring signal from detector 7 is therefore equal to the difference between temperature rise curve 21 and cooling curve 24. For quantitative absorption measurements the integral of this difference function, which is proportional to the radiation intensity, i.e. the area F between curves 21 and 24, is determined.

The area F can be determined by selecting a parallel to the zero line 22 as the integration base 25 and by determining the value of the time integral with reference to this base. The distance 26 of the integration base 25 from the zero line 22 is set on the basis of the requirement that the approximately triangular areas $F_1$ and $F_2$ formed essentially by the integration base 25 and curve section 24 be equal in value. Distance 26 may be set, for example, by impressing a direct voltage of selected value on the input of an integration member of the measuring value processor. Advisably, the absolute value of the voltage is then set so that, with a very high pressure in the measuring cuvette 4, the integral of area F becomes zero during the integration interval 27.

This simple measure permits, in addition to decoupling the measuring signals 21 superimposed on reference signals 20, an elimination of undesirable false light, which originates, for example, from the transmission or optical radiation capability of the filters 11 and 12 in a spectral range which cannot be absorbed by the gas under examination. This false light component is automatically compensated with the one-time setting of the direct voltage so that nonlinearities in the indication produced by the analyzer are avoided.

FIG. 2b shows the principle of separation of overlapping output signals from a radiation detector with full wave evaluation. Compared to the procedure explained in connection with FIG. 2a, this results in further improvement in the signal to noise ratio.

The integration base 28 for full wave evaluation is located below the output signal 20, 21 from detector 7, the integration limits are fixed by the points of intersection 30, 31, 32, 33, etc. of the output signal 20, 21 with the zero amplitude line 22. For evaluation the following differences are formed: $(F_1'-F_2')$ of the integrals $F_1'$, $F_2'$ of the reference signal and $(F_3'-F_4')$ of the integrals $F_3'$, $F_4'$ of the measuring signal. The value which would appear if a very high pressure were present in the measuring cuvette 4 $(F_{3p\infty}'-F_{4p\infty}')$ is subtracted from each one of the two differences so as to eliminate any false light influences and compensate for the effect produced by the signal overlapping.

$Fip_\infty$ are the areas that means integration values at infinetly high partial pressure. In practicel pressure is chosen so high that $Fip-Fip_\infty < 1\%$.

It is also possible to use the zero amplitude line 22 as the integration base. In that case it is necessary to form the sums of the areas lying above and below the zero amplitude line 22 for the reference signal 20 and for the measuring signal 21.

Figure 3:
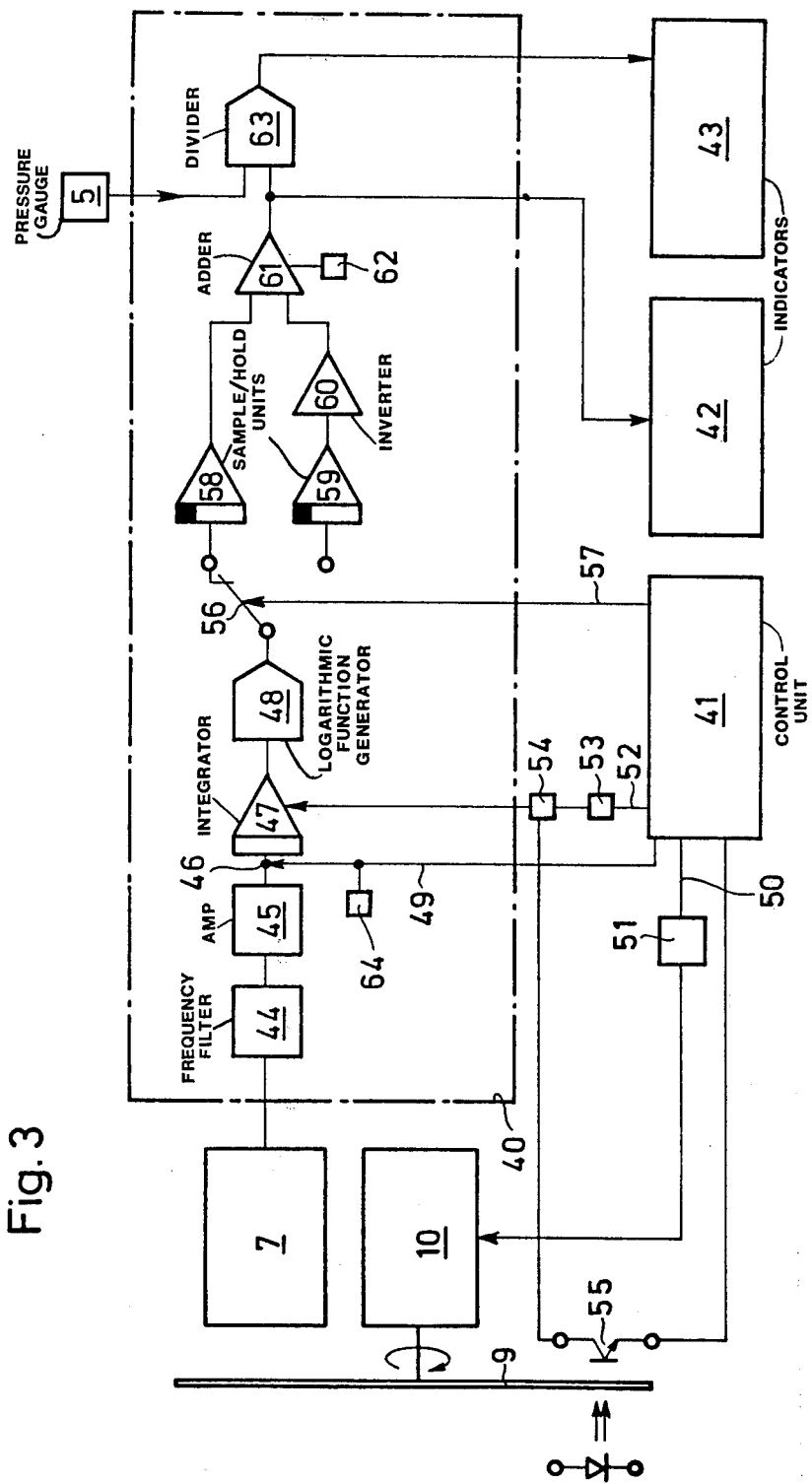
FIG. 3 is a block diagram of a circuit for effecting analog measuring value processing according to the invention.

A block circuit diagram for processing of the measuring values according to the method of the present invention, i.e. for determining the partial pressure and concentration of a measuring gas is shown in FIG. 3.

The measuring value processor 8 of FIG. 1 essentially includes an analog computer stage 40 and a digital control unit 41 which controls the functions of stage 40 and which is arranged together with a mains power portion, a first indicator unit 42 for the partial pressure and a second indicator unit 43 for the concentration, in a 19-inch housing. The output signal from the thermal detector 7 is delivered to a narrowbanded frequency filter 44 and an amplifier 45. The reference signals 20 and measuring signals 21 which appear alternatingly at the output 46 of the amplifier 45 are separately integrated in time succession by integration member 47, the integration values being converted to a logarithmic scale in a function generator 48 having a suitable characteristic. In order to set the spacing 26 or 29 of the integration base 25 or 28 from the zero line 22 to a predetermined value, a predetermined direct voltage is superimposed on the signal 20, 21 appearing at the output 46 of the amplifier 45. This direct voltage is supplied by an adjustable voltage source 64.

The signal supplied to line 49 operates an analog switch connecting 45 and 46 which determines start and stop of integration.

The control unit 41 essentially includes an oscillator with adjustable output frequency which actuates, via a second output 50 and a first frequency divider 51, the current supply for the motor 10 and, via a third output 52 and a second frequency divider 53 with series-connected counter 54, actuates integration member 47 and sets each integration interval to a predetermined value.

The start and stop of integration as shown by FIG. 3 is operated by the control unit 41.

The rotation of filter wheel 9 by motor 10 is monitored by a light barrier 55, the wheel being constructed to act on barrier 55 in a manner to cause the barrier to provide a signal which sets the counter 54 back to zero after each full rotation of the filter wheel 9. The connection between light barrier 55 and control unit 41 is a safety device to ensure that the control unit starts at identical status after each rotation of the chopper.

The function generator 48 is connected in series with an electronic switch 56 which is controlled via a fourth output 57 of the control unit 41 and transfers the direct output voltage associated with the reference signal 20 from unit 48 to a first sample/hold unit 58 and the direct output voltage associated with measuring signal 21 to a second sample/hold unit 59. The output of the first sample/hold unit 58 is connected directly with an adder stage 61, while the output of the second sample/hold unit 59 is connected with the adder stage 61 via an inverter 60, and the adder stage 61 forms a signal proportional to the difference between the two direct voltages. A calibrating member 62 adapts computer stage 40 to the respective gas being measured. Calibrating member 62 consists of an adder to add a constant value at zero partial pressure to make the difference between the outputs of the sample/hold units 58 and 59, zero. A multiplier increases the output signal in order to have calibrated partial pressure indication at the indicator 42.

The output of the adder stage 61 provides a signal representing the partial pressure of the gas being measured and is connected to indicator unit 42, and to the first input of a divider stage 63 which receives at its second input a signal representing the reading on pressure gauge 5 which measures the gas pressure in the measuring cuvette. Divider stage 63 forms a quotient between signal value from amplifier 61, proportional to the partial pressure of the gas component to be measured, and the signal value representing the total pressure of the total mixture in the measuring cuvette, and this quotient, representing the concentration of the gas component to be measured, is displayed by indicator unit 43 which is connected to the output of the divider stage 63.

The electronic signal processor acts as a lock-in amplifier since phase-locked summation of many time successive integrals is effected by the RC members of the sample/hold units 58 and 59, and the chopper frequency coincides with the center frequency of the narrowband amplifier 44, 45. The chopper frequency is equal to the filter wheel rotation rate multiplied by the number of filters on the wheel. An additional increase in the signal to noise ratio is realized by integration over the duration of each of the signal pulses from thermal detector 7. The basic component of control unit 41 is a quarz oscillator the pulses of which are given on programmable counter 54. The output of the counter controls via frequency divider 53, the analog switches of the computer stage to define start/stop operations of the integrator 47. The control unit consists of conventional TTL - and CMOS - integrated circuits respectively.

If the gas mixture contains a plurality of measuring gases and it is desired to monitor several or all of those gases, computer stage 40 can be provided with a plurality of assemblies each operated to monitor a respective measuring gas and each including respective first and second sample and hold units 58 and 59, a respective inverter 60, a respective adder stage 61, a respective calibrating member 62 and a respective divider stage 63.

Figure 4:
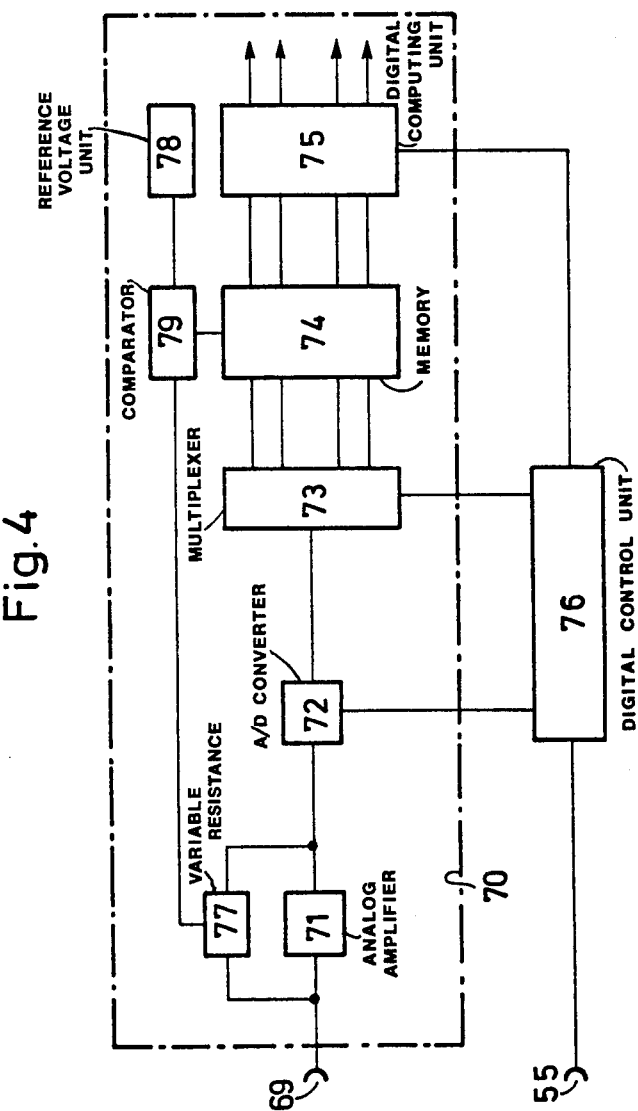
FIG. 4 is a block diagram of a circuit for effecting digital measuring value processing according to the invention.

The block circuit diagram of a digital measuring value processor for practicing the method, i.e. for determining the respective partial pressure and concentration of the measuring gas, is shown in FIG. 4.

In this processor, the analog signals present at the output 69 of the detector 7 are fed to a digital computer stage 70 and, via analog input amplifier 71 therein, to an integrating analog/digital converter 72. The digital integral signals are fed to a digital multichannel memory 74 via a time multiplexer 73. Each channel of memory 74 contains the results of integrations of the reference signal 20 or of the measuring signal 21, respectively, of a gas component to be measured in the gas mixture to be analyzed. Preferably, depending on the manner of computing the integral, the oldest value in each channel of memory 74 is replaced by a new one. In order to improve the signal to noise ratio, the values present in one memory channel are added together in a respective channel of a digital computing unit 75 and are processed further in a digital manner. Instead of an analog addition of a direct voltage present at the output of the preamplifier of the computing stage 70 as described in connection with FIG. 3, the computing unit 75 can add a digital constant automatically as determined once by the computing unit 75 for a very high pressure in the measuring cuvette 4. The entire circuit is monitored by a control unit 76.

In order to further improve the signal to noise ratio, the gain of the input amplifier 71 is automatically and continuously set by an electronically controllable variable resistance 77 so that the digital integrals of the reference signals remain constant in time. The regulation is effected by means of a reference voltage unit 78 and a comparator 79. This regulation can also be used for the analog version. Moreover, the multichannel memory 74 can be employed in the circuit according to FIG. 3 in the form of analog charge coupled device (CCD) memories. The unit 75 consists of a conventional micro processor (Intel 8080). The digital control 76 corresponds to the control unit shown in FIG. 3. The reference Voltage unit 78 and comparator 79 are conventional integrated circuits.

It will be understood that the above description of the present invention is susceptible to various modifications, changes and adaptations, and the same are intended to be comprehended within the meaning and range of equivalents of the appended claims.

What is claimed is:

1. In a method for determining the partial pressure and concentration of a measuring gas which is in mixture with at least one additional gas according to an optical absorption technique, which method includes producing a beam of light having a predetermined intensity, filtering the beam to alternatingly and cyclically give the light a first spectral distribution in which the light intensity will be reduced by passage through the measuring gas and a second spectral distribution in which the light intensity will not be reduced by passage through the measuring gas, passing the filtered beam through such a mixture, measuring the radiation intensity of the beam after passage through the mixture in a radiation detector having an active element which is heated by the radiation and which produces an output representative of its degree of heating, the output being composed of successive measuring signal segments, resulting from light having the first spectral distribution, alternating with successive reference signal segments, resulting from light having the second spectral distribution, and processing adjacent measuring signal and reference signal segments in order to compensate for fluctuations in the light beam being produced, variations in the light transmission and reflection properties of the beam path and other interference effects, the improvement wherein said step of processing comprises supplying the detector output to an input amplifier having a large signal to noise ratio, and compensating for signal inaccuracies due to superimposition of each signal segment portion produced by heating of the active element on a component representing the cooling behavior which the element would experience after the preceding heating period if further heating did not occur, said compensating step being performed by: integrating, in an integration member, each measuring signal occurring during a period when the element is being heated by the radiation, which integration is performed with respect to an integration base; applying to the integration member a direct voltage whose value determines the integration base; and adjusting the direct voltage to a magnitude which will cause the integral of a measuring signal, with respect to the integrator base, to have a value of zero when light having the first spectral distribution experiences maximum intensity reduction upon passage through such measuring gas.

2. A method as defined in claim 1 wherein the input amplifier is caused to have a large signal to noise ratio by being provided with a very high feedback resistance.

3. A method as defined in claim 1 wherein the input amplifier is caused to have a large signal to noise ratio by being provided with a high input impedance.

4. In a method for determining the partial pressure and concentration of a measuring gas which is in mixture with at least one additional gas according to an optical absorption technique, which method includes producing a beam of light having a predetermined intensity, filtering the beam to alternatingly and cyclically give the light a first spectral distribution in which the light intensity will be reduced by passage through the measuring gas and a second spectral distribution in which the light intensity will not be reduced by passage through the measuring gas, passing the filtered beam through such a mixture, measuring the radiation intensity of the beam after passage through the mixture in a radiation detector having an active element which is heated by the radiation and which produces an output representative of its degree of heating, the output being composed of successive measuring signal segments, resulting from light having the first spectral distribution, alternating with successive reference signal segments, resulting from light having the second spectral distribution, and processing adjacent measuring signal and reference signal segments in order to compensate for fluctuations in the light beam being produced, variations in the light transmission and reflection properties of the beam path and other interference effects, the improvement wherein said step of processing comprises supplying the detector output to an input amplifier having a large signal to noise ratio, and compensating for signal inaccuracies due to superimposition of each signal segment portion produced by heating of the active element on a component representing the cooling behavior which the element would experience after the preceding heating period if further heating did not occur, said compensating step being performed by: integrating, in an integration member, successive portions of the detector output with respect to an integration base which has a fixed value relative to the detector output value corresponding to a constant active element temperature, with the period of each integration being set by successive passage of the detector output through such values, thereby producing, cyclically and successively, a first integral corresponding in time to heating of the active element during a reference signal segment, a second integral corresponding in time to the respective succeeding cooling of the active element, a third integral corresponding in time to heating of the active element during the succeeding measuring signal segment, and a fourth integral corresponding in time to the respective succeeding cooling of the active element; determining the actual difference between the first and second integrals; determining the actual difference between the third and fourth integrals; determining the difference which would exist between the third and fourth integrals if the measuring gas were present at a very high pressure; and subtracting the difference which would exist from each of the actual differences.

5. A method as defined in claim 4 wherein the input amplifier is caused to have a large signal to noise ratio by being provided with a very high feedback resistance.

6. A method as defined in claim 4 wherein the input amplifier is caused to have a large signal to noise ratio by being provided with a high input impedance.

7. A method as defined in claim 4 wherein said step of integrating includes supplying said integration member with a direct voltage representing the integration base and giving the direct voltage a value such that the integration base is below the lowest detector output value.

8. A method as defined in claim 4 wherein said step of integrating includes supplying said integration member with a direct voltage representing the integration base and giving the direct voltage a value such that the integration base value is identical to the detector output value corresponding to a constant active element temperature.

9. In apparatus for determining the partial pressure and concentration of a measuring gas which is in mixture with at least one additional gas according to an optical absorption technique, which apparatus includes a light source producing a beam of light having a predetermined intensity, optical filter means arranged to filter the beam to alternatingly and cyclically give the light a first spectral distribution in which the light intensity will be reduced by passage through the measuring gas and a second spectral distribution in which the light intensity will not be reduced by passage through the measuring gas, a sample container arranged to contain such a gas mixture and disposed in the path of the filtered light beam beyond the filter means, a radiation detector disposed to receive the beam after passage through the container and having an active element which is heated by the radiation, the detector producing an output proportional to the degree of heating of the active element, the output being composed of successive measuring signal segments, resulting from light having the first spectral distribution, alternating with successive reference signal segments, resulting from light having the second spectral distribution, and means connected for processing adjacent measuring signal and reference signal segments in order to compensate for fluctuations in the light beam being produced, variations in the light transmission and reflection properties of the beam path and other interference effects, the improvement wherein said signal processing means are arranged for compensating for signal inaccuracies due to superimposition of each signal segment portion produced by heating of the active element on a component representing the cooling behavior which the element would experience after the preceding heating period if further heating did not occur, and include: an analog computer stage containing an input amplifier having a large signal to noise ratio and connected to receive the detector output; a digital control unit connected for controlling the operation of said computer stage; a first indicator unit connected to said computer stage for providing an indication of the partial pressure of the measuring gas in said container; and a second indicator connected to said computer stage for providing an indication of the concentration of the measuring gas in said container.

10. An arrangement as defined in claim 9 wherein said computer stage comprises: a frequency filter connected in series with said input amplifier; an integration member connected to receive the signals at the output of said amplifier and arranged to perform alternating separate integration of the reference signals and measuring signals appearing at the output of said amplifier; a function generator having a logarithmic characteristic function connected to the output of said integration member; an electronic switch having an input connected to the output of said function generator and having two outputs; first and second sample and hold units each connected to a respective output of said electronic switch, said switch being controlled by said control unit to deliver integration results relating to the reference signals to said first sample and hold unit and integration results relating to the measuring signal to said second sample and hold unit; an adder stage having a first input connected to the output of said first sample and hold unit; and an inverter connecting the output of said second sample and hold unit to a second input of said adder stage; a calibrating member connected to said adder stage for setting the result of the addition effected therein to represent the partial pressure of the measuring gas in said container; a divider stage having a first input connected to the output of said adder stage; and a pressure gauge connected to measure the gas pressure in said container and having a pressure signal output connected to a second input of said divider.

11. An arrangement as defined in claim 10 wherein said computer stage further comprises a direct voltage source connected to the input of said integration member for simultaneously matching said integration member and said input amplifier.

12. An arrangement as defined in claim 10 wherein there is a plurality of measuring gases in such mixture and said computer stage comprises a plurality of assemblies each for monitoring a respective measuring gas and each including respective first and second sample and hold units, a respective inverter, a respective adder stage, a respective calibrating member and a respective divider stage.

13. An arrangement as defined in claim 10 wherein: said digital control unit comprises an oscillator having a predetermined frequency output, a first frequency divider connected to the output of said oscillator, a second frequency divider connected to the output of said oscillator, and a counter connected between said second divider and said integration member; said digital control unit has a further output connected to said electronic switch for controlling switching thereof; said filter means are connected to be rotated by an electric motor; and said first divider is connected to control the movement of the motor.

14. An arrangement as defined in claim 13 further comprising means defining a light barrier connected to said counter and arranged to monitor movement of said filter means for resetting said counter to zero after each complete cycle of movement of said filter means.

15. In apparatus for determining the partial pressure and concentration of a measuring gas which is in mixture with at least one additional gas according to an optical absorption technique, which apparatus includes a light source producing a beam of light having a predetermined intensity, optical filter means arranged to filter the beam to alternatingly and cyclically give the light a first spectral distribution in which the light intensity will be reduced by passage through the measuring gas and a second spectral distribution in which the light intensity will not be reduced by passage through the measuring gas, a sample container arranged to contain such a gas mixture and disposed in the path of the filtered light beam beyond the filter means, a radiation detector disposed to receive the beam after passage through the container and having an active element which is heated by the radiation, the detector producing an output proportional to the degree of heating of the active element, the output being composed of successive measuring signal segments, resulting from light having the first spectral distribution, alternating with successive reference signal segments, resulting from light having the second spectral distribution, and means connected for processing adjacent measuring signal and reference signal segment in order to compensate for fluctuations in the light beam being produced, variations in the light transmission and reflection properties of the beam path and other interference effects, the improvement wherein said signal processing means are arranged for compensating for signal inaccuracies due to superimposition of each signal segment portion produced by heating of the active element on a component representing the cooling behavior which the element would experience after the preceding heating period if further heating did not occur, and include: a digital computer stage containing an input amplifier having a large signal to noise ratio and connected to receive the detector output; a digital control unit connected for controlling the operation of said computer stage; a first indicator unit connected to said computer stage for providing an indication of the partial pressure of the measuring gas in said container; and a second indicator connected to said computer stage for providing an indication of the concentration of the measuring gas in said container.

16. An arrangement as defined in claim 15 wherein said digital computer stage further includes an integrating analog/digital converter connected to the output of said amplifier, a multiplexer connected to the output of said converter, a digital multichannel memory connected to the output of said multiplexer, and a digital computer unit connected to the output of said memory.

17. Circuit arrangement as defined in claim 16 wherein said digital computer stage further includes an electronically controllable variable resistor connected to said amplifier for controlling the amplification factor of said amplifier, a reference voltage source, and a comparator connected between said reference voltage source and said resistor for controlling said resistor in a manner to maintain output signals from said converter corresponding to the integrals of the reference signal segments at a predetermined constant value.

18. An arrangement as defined in claim 16 wherein there is a plurality of measuring gases in such mixture said digital computer stage comprises a plurality of digital memories each associated with a respective one of the measuring gases.

19. An arrangement as defined in claim 16 wherein said digital computer unit is arranged to establish a predetermined integration base by addition of a digital constant to the digital representations of the measuring signals and the reference signals.

* * * * *